(12) United States Patent
Gainey, Jr. et al.

(10) Patent No.: US 8,777,171 B2
(45) Date of Patent: Jul. 15, 2014

(54) AIRBORNE PARTICLE AND MICROORGANISM COLLECTION SYSTEM

(75) Inventors: H. Johnny Gainey, Jr., Sunset Beach, NC (US); Randy Hardee, Sunset Beach, NC (US)

(73) Assignee: Smart Air Technologies LLC, Sunset Beach, NC (US)

( * ) Notice: Subject to any disclaimer, the term of this patent is extended or adjusted under 35 U.S.C. 154(b) by 559 days.

(21) Appl. No.: 13/077,243

(22) Filed: Mar. 31, 2011

(65) Prior Publication Data

US 2011/0239777 A1 Oct. 6, 2011

Related U.S. Application Data

(60) Provisional application No. 61/341,884, filed on Apr. 6, 2010.

(51) Int. Cl.
*A47B 96/06* (2006.01)
*E04G 5/06* (2006.01)

(52) U.S. Cl.
USPC ............. 248/231.71; 248/226.11; 248/227.3; 248/229.15; 248/228.6; 248/229.25

(58) Field of Classification Search
USPC ................... 248/689, 65, 72, 74.1, 74.4, 103, 248/226.11, 227.3, 229.15, 229.25, 228.6, 248/231.71
See application file for complete search history.

(56) References Cited

U.S. PATENT DOCUMENTS

| | | | | |
|---|---|---|---|---|
| 1,407,681 A | * | 2/1922 | Saunders | 248/103 |
| 1,478,921 A | * | 12/1923 | Slater | 248/231.71 |
| 1,554,118 A | * | 9/1925 | Moran | 248/103 |
| 1,688,765 A | * | 10/1928 | Veras | 248/103 |
| 1,900,691 A | * | 3/1933 | Carlson | 248/102 |
| 2,110,037 A | * | 3/1938 | De Rosa | 248/104 |
| 2,530,478 A | * | 11/1950 | Parent | 248/103 |
| 2,689,995 A | * | 9/1954 | Smith | 285/61 |
| 2,711,872 A | * | 6/1955 | Lampke | 248/103 |
| 3,298,648 A | * | 1/1967 | Sepanski | 248/103 |
| 4,666,111 A | * | 5/1987 | Schuler | 248/125.1 |
| 4,721,517 A | | 1/1988 | Cloutier | |
| 4,725,294 A | | 2/1988 | Berger | |
| 4,735,388 A | * | 4/1988 | Marks | 248/103 |
| 5,370,004 A | | 12/1994 | Bossart et al. | |
| 5,775,654 A | * | 7/1998 | Price | 248/231.61 |
| 6,056,246 A | * | 5/2000 | Argy, II | 248/103 |
| 6,125,710 A | | 10/2000 | Sharp | |
| 6,598,837 B1 | * | 7/2003 | Howard et al. | 248/103 |
| 6,729,587 B1 | * | 5/2004 | White | 248/72 |
| 7,155,988 B2 | | 1/2007 | Cole et al. | |
| 7,360,461 B2 | | 4/2008 | Desrochers et al. | |
| 7,377,188 B2 | | 5/2008 | Jenkins | |
| 2001/0041352 A1 | | 11/2001 | Reilly et al. | |
| 2002/0177236 A1 | | 11/2002 | Flappan | |
| 2004/0151617 A1 | | 8/2004 | Zanakis et al. | |
| 2004/0214260 A1 | | 10/2004 | Spiesman | |
| 2006/0173579 A1 | | 8/2006 | Desrochers et al. | |

* cited by examiner

*Primary Examiner* — Terrell McKinnon
*Assistant Examiner* — Michael McDuffie
(74) *Attorney, Agent, or Firm* — P. Jeff Martin; The Law Firm of P. Jeffrey Martin, LLC (57) ABSTRACT

A highly portable airborne particle and microorganism collection system which includes an air flow control mechanism adapted to control the air flow volume as air is pulled through the system via a vacuum source.

2 Claims, 6 Drawing Sheets

AIRBORNE PARTICLE AND MICROORGANISM COLLECTION SYSTEM

RELATED APPLICATIONS

This application claims the benefit of U.S. Provisional Application No. 61/341,884 filed on Apr. 6, 2010.

BACKGROUND OF THE INVENTION

1. Field of the Invention

The present invention relates generally to air sampling and testing equipment and, more particularly, to an airborne particle and microorganism collection system.

2. Description of the Related Art

Currently there exists in the art various airborne particle collection, sampling, and testing kits, devices, and systems. However, the prior art has failed to disclose or teach a highly portable system for collecting airborne particles and microorganisms which utilizes an adapter configured for use with a commercially-available vacuum source, the adapter being adapted to allow for a constant air flow pull volume rate of a selectively desired number of liters per minute, irrespective of selected vacuum source, in a manner which is quick, easy, and efficient.

Accordingly, a need exists for a portable system for collecting airborne particles and microorganisms which incorporates an adapter for use with any number of commercially-available vacuum sources. The development of the airborne particle and microorganism collection system fulfills this need.

A search of the prior art did not disclose any patents that read directly on the claims of the instant invention; however, the following references were considered related.

U.S. Pat. No. 4,721,517, issued in the name of Cloutier;
U.S. Patent Application no. 2004/0214260 A1, published in the name of Spiesman;
U.S. Pat. No. 5,370,004, issued in the name of Bossart et al.;
U.S. Pat. No. 4,725,294, issued in the name of Berger;
U.S. Pat. No. 6,125,710, issued in the name of Sharp;
U.S. Patent Application no. 2002/0177236 A1, published in the name of Flappan;
U.S. Pat. No. 7,155,988 B2, issued in the name of Cole et al.;
U.S. Patent Application no. 2004/0151617 A1, published in the name of Zanakis et al.;
U.S. Pat. No. 7,360,461 B2, issued in the name of Desrochers et al.;
U.S. Patent Application no. 2006/0173579 A1, published in the name of Desrochers et al.;
U.S. Patent Application no. 2001/0041352 A1, published in the name of Reilly et al.; and
U.S. Pat. No. 7,377,188 B2, issued in the name of Jenkins.

Consequently, a need has been felt for a highly portable airborne particle and microorganism collection system. This application presents claims and embodiments that fulfill a need or needs not yet satisfied by the products, inventions and methods previously or presently available. In particular, the claims and embodiments disclosed herein describe an airborne particle and microorganism collection system having at least one air particle and microorganism sample cassette, a first length of flexible tubing, a second length of flexible tubing, an adapter comprising an air flow control means, a compressible fitting, and a vacuum nozzle adapter, the system of the present invention providing unanticipated and nonobvious combination of features distinguished from the products, inventions and methods preexisting in the art. The applicant is unaware of any product, method, disclosure or reference that discloses the features of the claims and embodiments disclosed herein.

SUMMARY OF THE INVENTION

Briefly described according to one embodiment of the present invention, an airborne particle and microorganism collection system is provided for collecting airborne particles and microorganisms, the air particles and microorganisms may be allergenic, pathogenic, and/or toxigenic, and include but are not limited to bacteria, viruses, bacterial spores, mold spores, fungi, cellulose fibers, fiberglass particulates, insect fragments, and pollen. The system of the present invention comprises an air particle and microorganism sample cassette for collecting airborne particles and microorganisms, the sample cassette having an air intake and a media defining a collection surface to which air particles and microorganisms are collected.

A vacuum source draws sampled air through the air intake of the sample cassette. The vacuum source may include a filtered containment bag for dust collection. The vacuum source may also include a versatile air diffuser to restrict outflow of air from the vacuum source to prevent undesired particle blockage.

The sample cassette includes an inlet to which one end of a first length of flexible tubing is removably connected. The opposing end of the first length of flexible tubing is removably connected to an inlet port of an adapter.

The adapter is defined as a valve comprising the inlet port, an outlet port, and an air flow control mechanism.

A second length of flexible tubing is provided having one end removably connected to the outlet port of the adapter. The opposing end of the second length of flexible tubing is removably connected to a compressible fitting. The compressible fitting is adapted for removable, airtight sealable connection to the inlet port of a vacuum nozzle adapter.

The vacuum nozzle adapter is adapted for airtight sealable connection to a hose portion of the vacuum source. The vacuum nozzle adapter includes an outlet port to which the mouth of the hose portion of the vacuum source is removably connected. The sample cassette is in fluid communication with the vacuum source via an airtight sealable interconnection by the first length of flexible tubing, adapter, second length of flexible tubing, vacuum nozzle adapter, and vacuum source.

The air flow control mechanism is adapted to control the air flow volume as air is pulled through the system via the vacuum source. The air flow control mechanism is adapted to maintain a constant air flow pull volume rate of a selectively desired number of liters, i.e., 5 liters, 10 liters, or 15 liters, per minute. The air flow control mechanism may be mounted to the vacuum nozzle adapter or may be included as an integral component of a vacuum source.

In accordance to one embodiment of the present invention, the system may include a vacuum rate indicator for displaying the air flow pull volume rate of air as air is being pulled through the system.

In accordance to another embodiment of the present invention, the system may include a vacuum source having an air flow control mechanism for adjustably controlling the electrical energy supplied by the vacuum source.

A support mechanism is provided for supporting the sample cassette and the first length of flexible tubing in an elevationally-suspended manner above the ground during a sample collection interval. The support mechanism comprises a linearly elongated rod having an upper end opposing a lower end. The upper end of rod includes an annular pin mounted thereto, the pin having an eye through which the upper end of the first length of flexible tubing passes and is supported thereby. The lower end of rod includes a flexible clamp mounted thereto for tightly receiving and holding a semi-rigid bracket therein.

The bracket, in accordance to one embodiment, is adapted for engaging an object, such as a door edge, table edge, or chair. A threaded aperture is defined through the bracket for threadedly receiving a thumb screw. In order to ensure bracket remains in a fixedly engaged position with object (i.e., door edge), the thumb screw is threaded through threaded aperture of bracket until shank of thumb screw contacts object.

In order to facilitate collection of airborne particle and microorganism samples from inside a motor vehicle, a seal mechanism is provided. The seal mechanism comprises an elongated configuration constructed of a resiliently compliant material. An upper surface of seal mechanism includes an elongated slit adapted to snugly receive and conform to an outer window edge of a motor vehicle. The seal mechanism further comprises an aperture defined through a sidewall thereof, wherein the aperture allows the first length of flexible tubing to be inserted therethrough. In accordance to still another embodiment, the system of the present invention includes a timing device integrated therewith. This embodiment may further include an environmental sensor(s) for detecting and/or measuring relevant environmental factors such as humidity, current time, pressure, and temperature.

In accordance to yet another embodiment, the system of the present invention may include sensors which communicate with a control to cause a sample to be collected in response to an event that is detected by the sensors. Such a system might be equipped with a mold spore monitor, and when levels of mold spores achieve a predetermined level, a controller can be programmed to initiate a sampling event, to actuate vacuum source to collect samples on the collection surface of sample cassette for later analysis in response to the sensor readings. Such sensors can be used to measure relevant environmental factors. Based on the detection of a specific environmental factor by such a sensor, or in accord with a sampling protocol programmed into the control, various functions may be executed by the control. Such functions include: record generation of the environmental conditions at the time of detection; operation control of any system components whose performance depends on a measured environmental parameters; manipulation of a programmed sampling protocol based on measured environmental factors; and production of an alert signal to notify an operator or user of an important change in the environmental conditions (as determined by programmed control parameters). A timer may be included to provide a timing signal to the control.

The system of the present invention is envisioned to be made commercially available as a kit, wherein the kit comprises a package for housing a number of sample cassettes, a first length of flexible tubing, an adapter, a second length of flexible tubing, a fitting, a vacuum nozzle adapter, and an instruction leaflet.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENT

Detailed Description of the Figures

Referring now to FIGS. 1, 2, 3, and 4, an airborne particle and microorganism collection system 10 is shown, according to one embodiment of the present invention. The airborne particle and microorganism collection system 10, hereinafter referred to as "system 10", comprises an air particle and microorganism sample cassette 20 for collecting airborne particles and microorganisms, the sample cassette 20 having an air intake 21 and a media 23 defining a collection surface 23a to which air particles and microorganisms are collected. The system 10 is designed and configured for the collection of air particle and microorganism samples, some of the air particles and microorganisms may be allergenic, pathogenic, and/or toxigenic and include bacteria, viruses, bacterial spores, mold spores, fungi, cellulose fibers, fiberglass particulates, insect fragments, and pollen.

Figure 1:
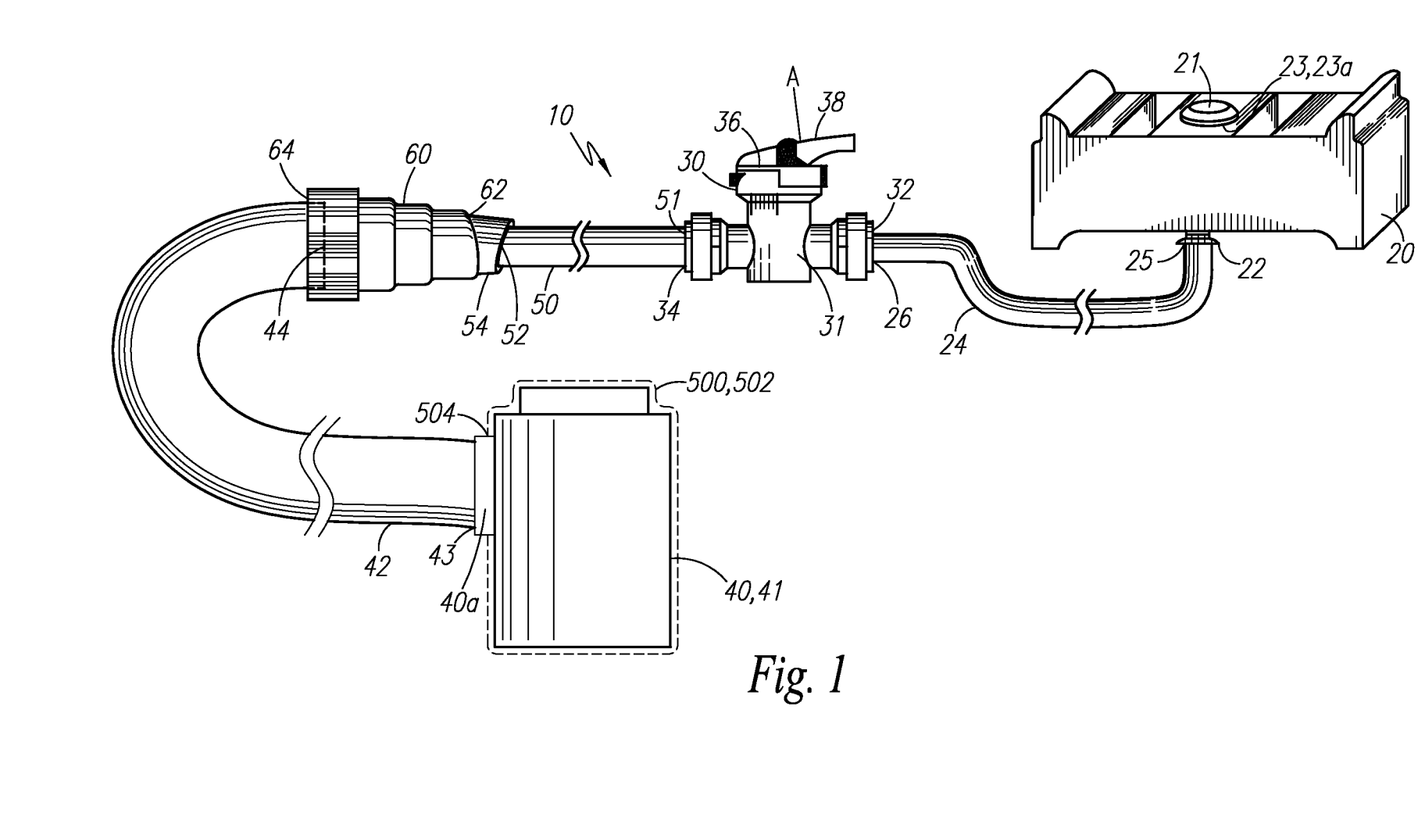
FIG. 1 is a perspective view of the airborne particle and microorganism collection system, shown fully assembled, according to one embodiment of the present invention.
Figure 1A:
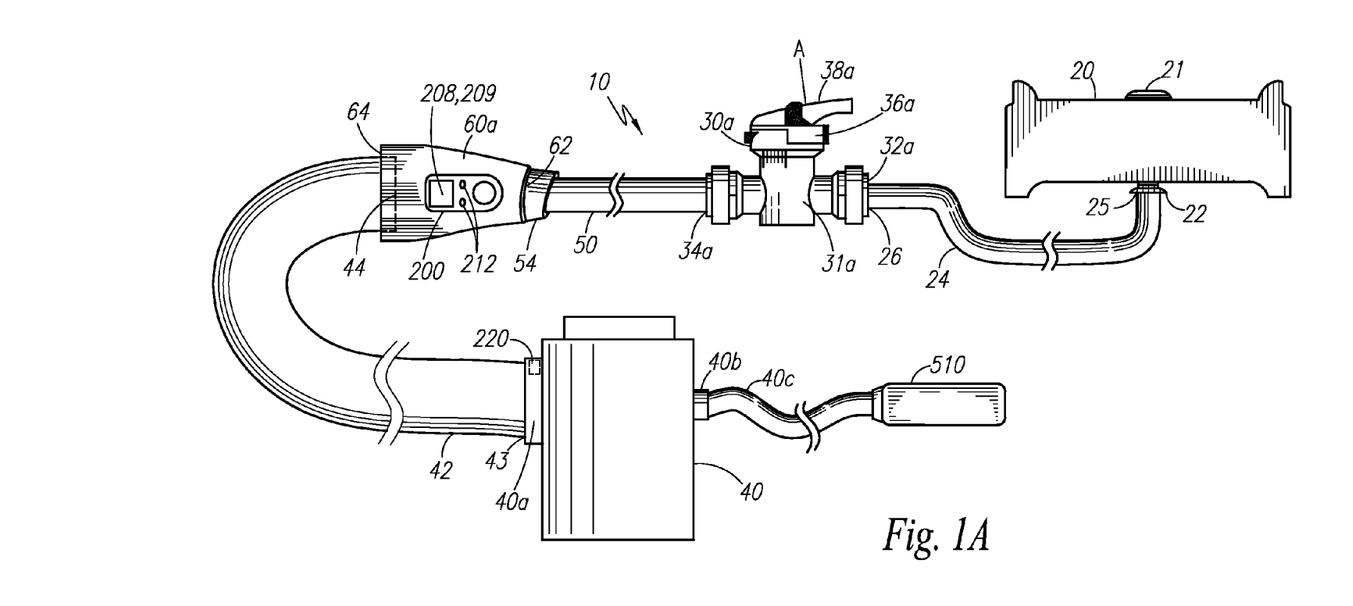
FIG. 1A is a perspective view of the airborne particle and microorganism collection system, shown fully assembled, according to an alternate embodiment of the present invention.

Sampled air is drawn in through the air intake 21 of the sample cassette 20 by the action of a vacuum source 40. The vacuum source 40 includes a flexible vacuum hose 42 having an outlet 43 and an inlet 44, the outlet 43 is in fluid communication with an inlet port 40a of vacuum source 40. The vacuum source 40 is selected from the group which includes but is not limited to commercially-available vacuum pump devices which supply the following units of peak power, electric current, or electric potential: 1.0 hp, 3.5 hp, 4.5 hp, 5.0 hp, 6.0 hp, 7.0 amperes, 10.0 amperes, 10.5 amperes, 11.0 amperes, 12.0 amperes, 12.0 volts, and 24.0 volts. One such example of a commercially-available vacuum pump device 41 is the Shop-Vac® HANGUP MINI®, manufactured and owned by Shop Vac Corporation, and supplying 1.0 peak hp. For purposes of the present invention, the commercially-available vacuum pump devices are intended to include inflation and deflation pump devices. The vacuum source 40 may include a filtered containment bag 500 for dust collection. The filtered containment bag 500 comprises a lightweight enclosure 502 having an open bottom and an inlet port slit or opening 504, the bag 500 being sized and shaped to cover the vacuum source 40. The vacuum source 40 may also include a versatile air diffuser 510 to restrict outflow of air from the exhaust port 40b of vacuum source 40 in order to prevent undesired particle dispersion and blockage, and thereby eliminating inaccurate sample results. The diffuser 510 may be attached to an end of a flexible hose 40c connected to exhaust port 40b, as shown in FIG. 1A. Alternatively, diffuser 510 may be connected to exhaust port 40b.

The sample cassette 20 includes an inlet 22 to which one end 25 of a first length of flexible tubing 24 is removably connected so as to form an airtight seal. The first length of flexible tubing 24 preferably defines an outer diameter measuring ⅜ inch and an inner diameter measuring ¼ inch.

Figure 2:
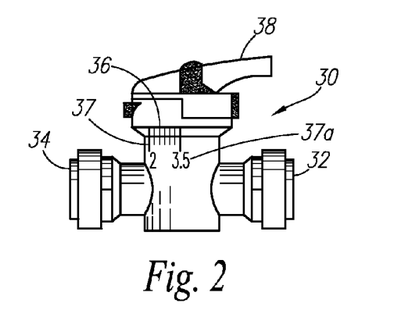
FIG. 2 is a side elevational view of the adapter of FIG. 1, according to one embodiment of the present invention.

The first length of flexible tubing 24 has an opposing end 26 removably connected to an inlet port 32 of an adapter 30, wherein the connection by the opposing end of the first length of flexible tubing 24 to the inlet port 32 is an airtight sealed connection. The adapter 30 is defined as a straight valve 31 comprising the inlet port 32, an outlet port 34, and an air flow control mechanism 36 for controlling air flow volume as air is pulled through straight valve 31. The first length of flexible tubing 24 is fluid communication with the adapter 30.

A second length of flexible tubing 50 is provided having one end 51 removably connected to the outlet port 34 of adapter 30, wherein the connection by the one end 51 of the second length of flexible tubing 50 is an airtight sealed connection. The second length of flexible tubing 50 preferably defines an outer diameter measuring ⅜ inch and an inner diameter measuring ¼ inch.

Figure 4:
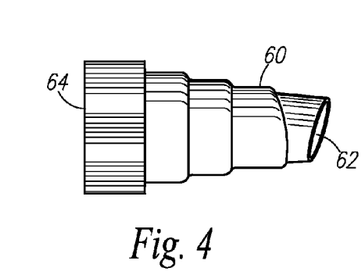
FIG. 4 is a side elevational view of the vacuum nozzle adapter of FIG. 1, according to one embodiment of the present invention.
Figure 5:
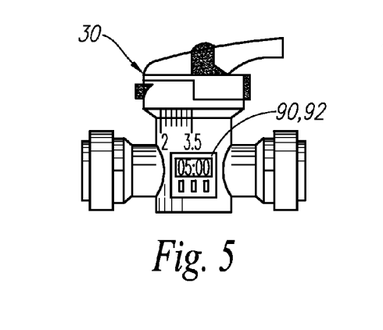
FIG. 5 is a side elevational view of a timer integrated with the present invention, according to an alternate embodiment thereof.

The second length of flexible tubing 50 has an opposing end 52 removably connected in an airtight sealed fashion to a compressible fitting 54. The compressible fitting 54 is preferably defined as having a conical shape. The compressible fitting 54 is adapted for removable, airtight sealable connection to the inlet port 62 of a vacuum nozzle adapter 60. The vacuum nozzle adapter 60 defines an elongated, tubular configuration constructed of either a rigid, or semi-flexible, lightweight material. The vacuum nozzle adapter 60 is adapted for removable, airtight sealable connection to the flexible vacuum hose 42 of the vacuum source 40. More specifically, the vacuum nozzle adapter 60 includes an outlet port 64 to which the inlet 44 of the hose 42 of vacuum source 40 is removably connected in an airtight sealed fashion, the inlet 44 of hose 42 being in fluid communication with the outlet port 64. The sample cassette 20 is in fluid communication with the vacuum source 40 via the airtight sealable interconnection by the first length of flexible tubing 24, adapter 30, second length of flexible tubing 50, vacuum nozzle adapter 60 and hose 42 of vacuum source 40, the adapter 60 positioned between the sample cassette 20 and vacuum source 40.

The air flow control mechanism 36 of adapter 30 provides unanticipated and nonobvious functional features and advantages. The air flow control mechanism 36 is adapted to control the air flow volume as air is pulled through the system 10 via the vacuum source 40, the air flow control mechanism 36 being adapted and configured to maintain a constant air flow pull volume rate of 5 liters per minute when interconnected with remaining elements comprising the system 10 of the present invention and when using any commercially-available vacuum source 40. It is envisioned the air flow control mechanism 36 may be designed, configured, and manufactured in a number of models so as to provide a constant air flow pull volume rate according to consumer need and preference.

The air flow control mechanism 36 includes a power indicator gauge 37, wherein the gauge 37 comprises indicia 37a disposed as units of power, electric current, or electric potential, such as, but not limited to 1.0 hp, 3.5 hp, 4.5 hp, 5.0 hp, 6.0 hp, 7.0 amperes, 10.0 amperes, 10.5 amperes, 11.0 amperes, 12.0 amperes, 12.0 volts, and 24.0 volts. For purposes of this disclosure, the term "electrical energy" comprises power, electric current, and electric potential. The indicia 37a or units correspond to the power, electric current, or electric potential supplied by commercially-available vacuum pump devices. The air flow control mechanism 36 further includes an actuator A, shown herein as a lever 38 or dial, for controlling air flow volume through straight valve 31. The lever 38 is turnable so as to correspond to the particular unit of power, electric current, or electric potential supplied by the commercially-available vacuum pump device selected by operator, thereby ensuring air flow control mechanism 36 maintains a constant air flow pull volume rate of 5 liters per minute. Turning lever 38 to an electrical energy unit consistent with the electrical energy supplied by selected vacuum source 40 opens straight valve 31 to a degree providing for an air flow volume rate of 5 liters per minute. For example, in the event operator possesses a vacuum pump device 40 having a peak power measure of 1.0 hp, in order to ensure the air flow control mechanism 36 maintains a constant air flow pull volume rate of 5 liters per minute, operator turns lever 38 so that lever 38 points to or indicates 1.0 hp on the gauge 37.

By way of another example, in the event operator possesses a vacuum pump device having a power measure of 3.5 hp, in order to ensure the air flow control mechanism 36 maintains a constant air flow pull volume rate of 5 liters per minute, operator turns lever 38 so that lever 38 points to or indicates 3.5 hp on the gauge.

By way of further example, in the event a consumer/operator has a vacuum source 40 supplying an electric current of 12.0 amperes and requires the air flow control mechanism 36 to maintain a constant air flow pull volume rate of 10 liters per minute, the air flow control mechanism 36 is designed, configured, and manufactured as an alternative, commercially-available model, such that in order to ensure the air flow control mechanism 36 of the alternative model maintains a constant air flow pull volume rate of 10 liters per minute, operator simply turns lever 38 so that lever 38 points to or indicates 12.0 amperes on the gauge.

Referring now to FIGS. 1A-1C, and 2A, in accordance to an alternate embodiment of the present invention, adapter 30a is defined as a straight valve 31a comprising an inlet port 32a, an outlet port 34a, and an adjustable air flow control mechanism 36a for controlling air flow volume through straight valve 31a. The adjustable air flow control mechanism 36a includes an actuator A, shown herein as a lever 38a or dial, being turnable for controlling air flow volume through straight valve 31a. The lever 38 allows the operator to manually adjust air flow pull volume rate to a selectively desired rate, e.g. 15 liters per minute.

Figure 1B:
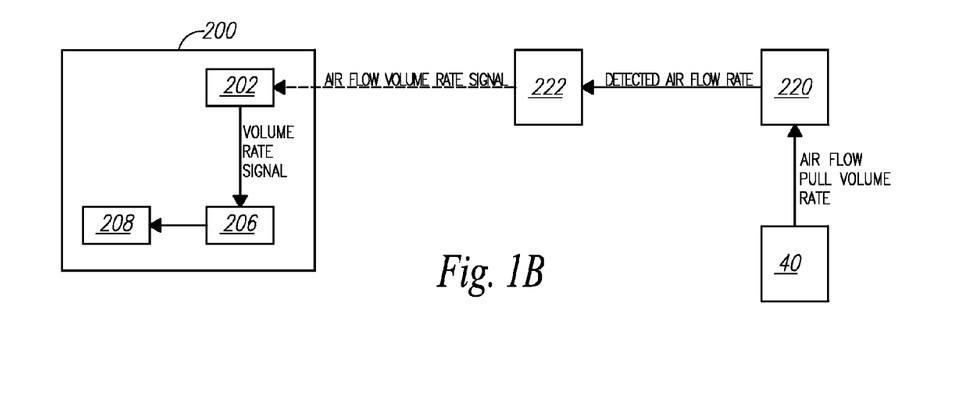
FIG. 1B is a detailed block diagram of an air flow measurement circuit, according to one embodiment of the present invention.
Figure 1C:
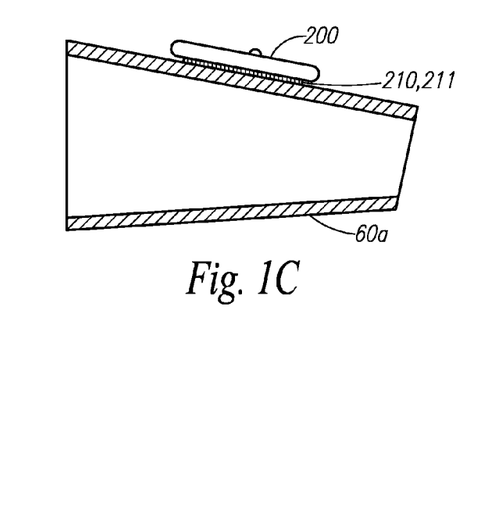
FIG. 1C is a side cross-sectional view of a vacuum nozzle adapter illustrating a vacuum rate indicator removably attached to an outer surface thereof, according to one embodiment of the present invention.

In further accordance to this particular embodiment, a vacuum rate indicator 200 is provided for displaying the air flow pull volume rate of air as air is being pulled through the system 10, the air flow pull volume rate is directly proportional to the air flow control mechanism 36a setting. The indicator 200 is shown fixedly attached to a vacuum nozzle adapter 60a, but may be adapted for removable attachment via a suitable fastening means 210, such as a hook and loop fastening system 211. Such feature allows operator to position the indicator 200 in a selectively desired, prominent location about the system 10, such as to a housing of the vacuum source 40, thereby allowing operator to quickly, easily, and efficiently monitor the indicator 200 during operation thereof.

The vacuum rate indicator 200 comprises a receiver 202 for wirelessly receiving signals transmitted via an air flow rate sensor 220. The air flow rate sensor 220 is suitably disposed along an inner circumferential sidewall of inlet port 40a of vacuum source 40. The sensor 220 detects the air flow pull volume rate as air is pulled through the system 10 via the vacuum source 40. The sensor 220 communicates detected air flow volume rate to a transceiver 222 being in connection therewith, the transceiver 222 transmits wirelessly an air flow volume rate signal received by a transceiver 202 in connection with indicator 200. Transceiver 202 of indicator 200 transmits the received air flow volume rate signal to an indicator drive 206 in connection with transceiver 202, the indicator drive 206 enables the air flow volume rate signal to be displayed on a display panel 208 as an air flow volume rate measure, e.g. 15 liters per minute. The display panel 208 is shown in FIG. as a liquid crystal display (LCD) display panel 209; however, other display panels 208 are envisioned, such as a light-emitting diode (LED) display panel (not shown). The air flow volume rate is preferably displayed by display panel 208 as a measure of liters per minute; however, other units of measure are envisioned, such as feet per sec (fps).

The vacuum rate indicator 200 may comprise a plurality of control switches 212 or buttons for facilitating operational functions thereof, such as powering the indicator 200 on and off and resetting the indicator 200.

Figure 2A:
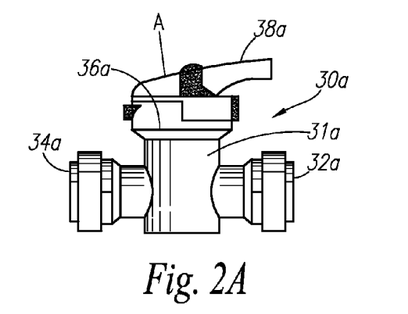
FIG. 2A is a side elevational view of an adapter, according to an alternate embodiment of the present invention.
Figure 2B:
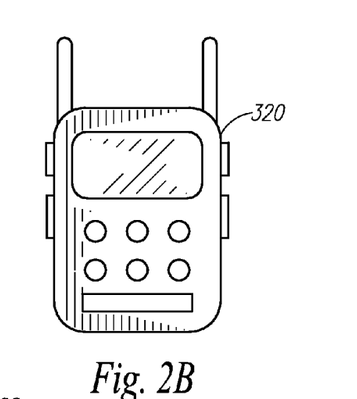
FIG. 2B is a perspective view of an environmental sensor, according to one embodiment of the present invention.
Figure 3:
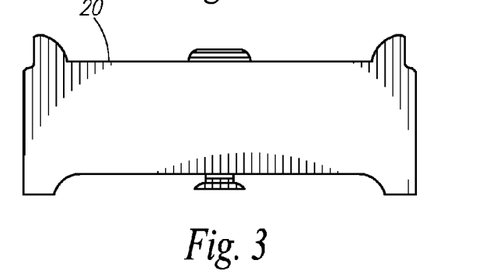
FIG. 3 is a side elevational view of the sample cassette of FIG. 1, according to one embodiment of the present invention.

During operation of this particular embodiment, the vacuum rate indicator 200 allows the operator to manually adjust the air flow pull volume rate via lever 38a to a selectively desired rate, e.g., 15 liters per minute. Once vacuum source 40 is powered on, operator turns or adjusts lever 38a directionally (clockwise or counterclockwise) until a desired measure or number of unit(s) of air flow pull volume is achieved. Thus, while monitoring the vacuum rate indicator 200, operator simply adjusts the lever 38a as is necessary until an air flow pull volume rate measure coordinates with operator's desired air flow pull volume rate.

Figure 1D:
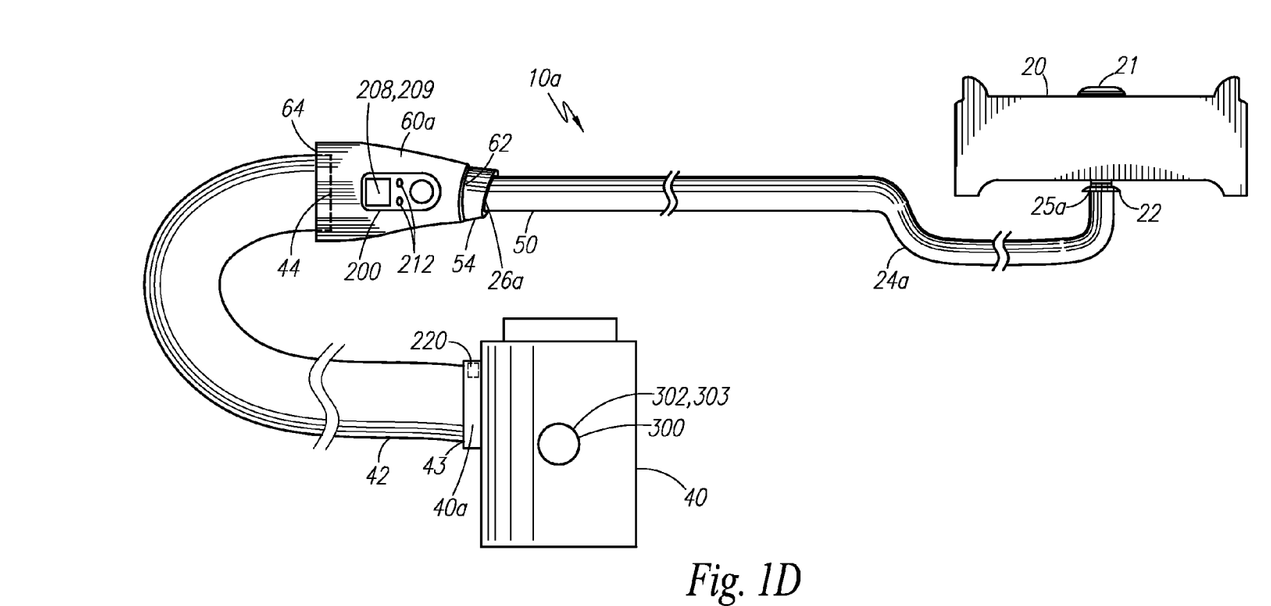
FIG. 1D is a perspective view of the airborne particle and microorganism collection system, shown fully assembled, according to another alternate embodiment of the present invention.

Referring now to FIG. 1D, in accordance to still another alternate embodiment of the present invention, the airborne particle and microorganism collection system 10a comprises at least one air particle and microorganism sample cassette 20, a vacuum source 40, a length of flexible tubing 24a, a compressible fitting 54, a vacuum nozzle adapter 60a, and a vacuum rate indicator 200, wherein the vacuum source 40 comprising an air flow control mechanism 300.

Sampled air is drawn in through the air intake 21 of the sample cassette 20 by the action of a vacuum source 40. The vacuum source 40 includes a flexible vacuum hose 42 having an outlet 43 and an inlet 44, the outlet 43 is in fluid communication with an inlet port 40a of vacuum source 40. The sample cassette 20 includes an inlet 22 to which one end 25a of a length of flexible tubing 24a is removably connected so as to form an airtight seal. The flexible tubing 24a has an opposing end 26a removably connected in an airtight sealed fashion to a compressible fitting 54. The compressible fitting 54 is adapted for removable, airtight sealable connection to the inlet port 62 of a vacuum nozzle adapter 60a. The vacuum nozzle adapter 60a defines an elongated, tubular configuration constructed of either a rigid, or semi-flexible, lightweight material. The vacuum nozzle adapter 60a is adapted for removable, airtight sealable connection to the flexible vacuum hose 42 of the vacuum source 40. More specifically, the vacuum nozzle adapter 60a includes an outlet port 64 to which the inlet 44 of the hose 42 of vacuum source 40 is removably connected in an airtight sealed fashion, the inlet 44 of hose 42 being in fluid communication with the outlet port 64. The sample cassette 20 is in fluid communication with the vacuum source 40 via the airtight sealable interconnection by the flexible tubing 24a, vacuum nozzle adapter 60a and vacuum source 40, the adapter 60a positioned between the sample cassette 20 and vacuum source 40.

The air flow control mechanism 300 comprises an adjustable, electrical energy setting control 302 adapted and configured for adjustably controlling the electrical energy (power, electric current, or electric potential) supplied by vacuum source 40, and thereby adjustably controlling the air flow pull volume rate, the air flow pull volume rate being directly proportional to the air flow control mechanism 300 setting. The setting control 302 is shown herein as a turnable knob 303; however, other setting control 302 devices are envisioned which include, but are not limited to a lever, switch, toggle bat, rocker arm, and the like. The air flow control mechanism 300 is electrically coupled to and in operative, electrical communication with the electrical energy generation means (not shown) of vacuum source 40, the air flow control mechanism 300 is adapted and configured to modulate the electrical energy supplied by vacuum source 40. Thus, the electrical load supplied by electrical energy generation means of vacuum source 40 is increased or decreased via manipulation, e.g. turning, of setting control 302. The air flow control mechanism 300 functions to allow an operator of the system 10a to manually adjust the air flow pull volume rate to a selectively desired rate, e.g. 5 liters per minute or 15 liters per minute. While monitoring the vacuum rate indicator 200, operator simply adjusts the air flow control mechanism 300 as is necessary until an air flow pull volume rate measure coordinates with operator's desired air flow pull volume rate.

Figures 6, 7:
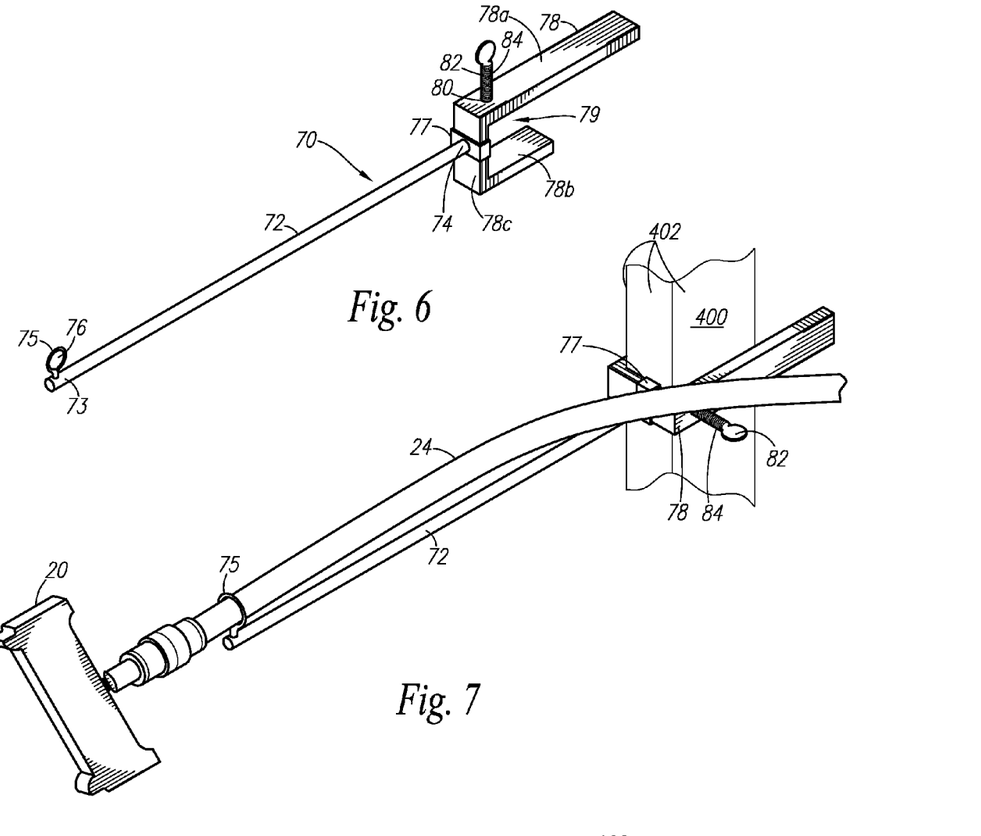
FIG. 6 is a perspective view of a support mechanism, according to one embodiment of the present invention.
FIG. 7 is partial perspective view illustrating the tubing and sample cassette supported in an elevationally-suspended manner above the ground by the support mechanism, according to one embodiment of the present invention.

Referring now to FIGS. 6-7, a support mechanism 70 is disclosed for supporting the sample cassette 20 and the first length of flexible tubing 24 in an elevationally-suspended manner above the ground during a sample collection interval. The support mechanism 70 comprises a linearly elongated rod 72 having an upper end 73 opposing a lower end 74. The upper end 73 of rod 72 includes an annular pin 75 mounted thereto, the pin 75 having an eye 76 serving as a guide 75 through which the upper end 25 of the first length of flexible tubing 24 passes and is supported thereby. The lower end 74 of rod 72 includes a flexible clamp 77 mounted thereto for tightly receiving and holding a semi-rigid bracket 78 therein via mechanical interference.

The bracket 78 comprises a long horizontal member 78*a* integrally joining a short horizontal member 78*b* by a vertical member 78*c*, thereby forming an object receiving cavity 79. The long member 78*a* includes a threaded aperture 80 defined therethrough for threadedly receiving a thumb screw 82 having an elongated threaded shank 84. An object, such as the edges 402 of a door 400, is received in the object receiving cavity 79 of bracket 78 in a snug, frictional-fit manner, so as to maintain bracket 78 in a removably fixed position. In order to ensure bracket 78 remains in a fixedly engaged position with object (door edges 402), the thumb screw 82 is threaded through threaded aperture 80 of long member 78*a* until shank 84 of thumb screw 82 contacts object. Because thumb screw 82 is provided with an elongated shank 84, the shank 84 also provides a support surface upon which the first length of flexible tubing 24 rests, as shown in FIG. 7.

Referring now more particularly to FIGS. 1, 8, and 9A-9C, in order to facilitate collection of airborne particle and microorganism samples from inside a motor vehicle 130, a seal mechanism 100 is provided. The seal mechanism 100 comprises an elongated configuration constructed of a resiliently compliant material, such as foam. An upper surface of seal mechanism 100 includes an elongated slit 102 extending a longitudinal length theredown. The slit 102 is adapted to snugly receive and conform to a door outer window edge 132 of a motor vehicle 130.

Figure 8:
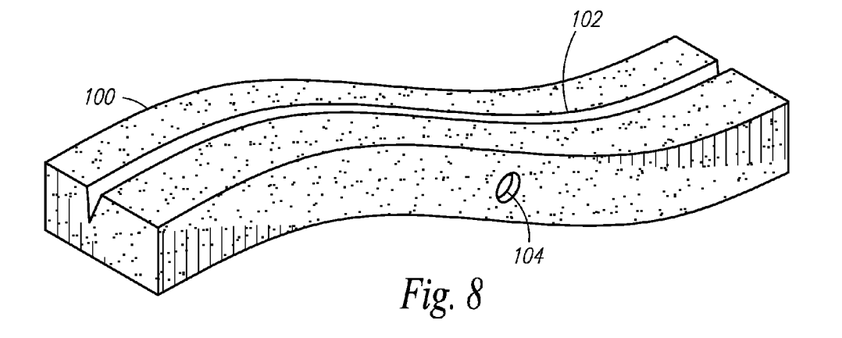
FIG. 8 is perspective view of a seal mechanism, according to one embodiment of the present invention.
Figures 9A, 9B:
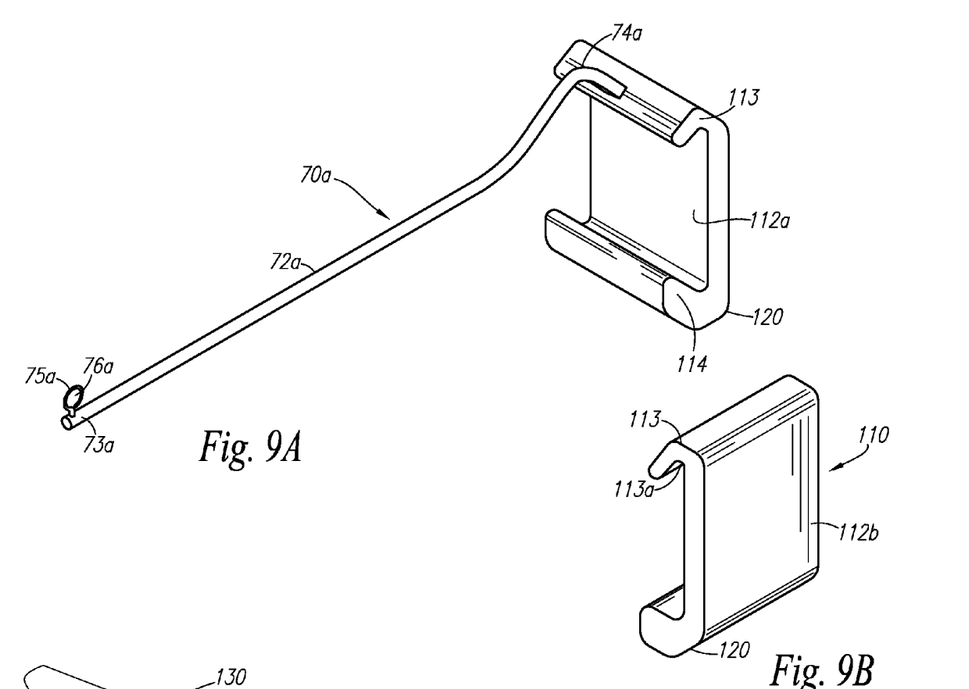
FIG. 9A is a perspective view of a support mechanism and support bracket, according to an alternate embodiment of the present invention.
FIG. 9B is a rear perspective view of the support bracket illustrated in FIG. 9A.
Figure 9C:
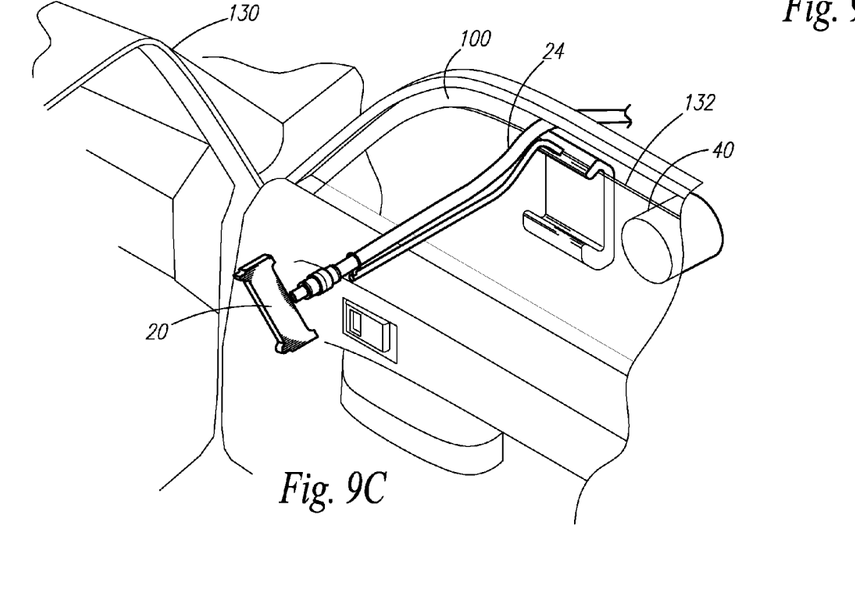
FIG. 9C is a perspective view of the support mechanism and support bracket of FIG. 9A shown in use.

The seal mechanism 100 further comprises an aperture 104 defined through a lateral sidewall thereof, transverse to slit 102, wherein the aperture 104 allows the first length of flexible tubing 24 to be inserted therethrough. The aperture 104 further provides a means of support for the first length of flexible tubing 24. After inserting the first length of flexible tubing 24 through aperture 104, the first end of the first length of flexible tubing 24 is removably connected to the outlet of a sample cassette 20 so as to form an airtight seal therebetween. The seal mechanism 100 is then positioned such that the slit 102 thereof engages intimately the entire outer edge 132 of the vehicle 130 window. The window is then raised until the seal mechanism 100 forms a seal around the vehicle 130 window frame.

Referring now more specifically to FIGS. 2B, and 9A-9C, in accordance to another alternate embodiment of the present invention, support mechanism 70*a* comprises a linearly elongated rod 72*a* having an upper end 73*a* opposing a lower end 74*a*. The upper end of rod 72*a* may include an annular pin 75*a* mounted thereto, the pin 75*a* having an eye 76*a* serving as a guide 75*a* through which the upper end 73*a* of the first length of flexible tubing 24 passes and is supported thereby. The lower end 74*a* of rod 72*a* is curved so as to define an arcuate shape and is mounted or molded integral to a support bracket 110.

The support bracket 110 comprises a generally planar body 112 having a front surface 112*a* opposing a rear surface 112*b*, and an upper horizontal, incurvate edge 113 and a lower horizontal, incurvate edge 114. The upper horizontal, incurvate edge 113 forms a window edge receiving cavity 113*a*. The window edge receiving cavity 113*a* is adapted to receive the outer window edge 132 of a motor vehicle 130 in a snug fit manner. The lower horizontal, incurvate edge 114 forms a bulbous abutment 114*a* for engagement against an outer surface of a window of a motor vehicle. The rear surface 112*b* and lower horizontal, incurvate edge 114 are joined integrally by a flat interface 120. The support bracket 110 is constructed of a flexible, semi-soft rubber or plastic material, the construction material preferably being a non-skid material facilitating frictional grip to the window, and which prevents scratches and other damage to the motor vehicle window during installation and use. After positioning support bracket 110 on window edge 132 of motor vehicle 130, the seal mechanism 100 is engaged against the outer window edge 132 of the motor vehicle 130 as described hereinabove, and such that a portion of the slit 102 of seal mechanism 100 receives the upper horizontal, incurvate edge 113 of support bracket 110.

Airborne particle and microorganism collection samples should be collected in at least two locations, namely inside the residence or structure and outdoors. The outdoor sample provides a control sample against which the indoor sample may be evaluated to determine if an unusual mold elevation is present inside the residence or structure and the degree of elevation. Thus, it is imperative that the sampling interval for each location be of equal timing. Therefore, in order to make certain samples were collected in both locations under equal timing, operator is required to utilize a timing device, such as a stop watch or wrist watch.

In addition, it is imperative that environmental conditions are measured via at least one environmental sensor 320 prior to collection of each sample(s). The environmental sensor(s) 320 is adapted for detecting and/or measuring relevant environmental factors such as humidity, current time, pressure, and temperature.

Once the system 10 of the present has been assembled and is stationed in a desired location, i.e., inside the residence, operator powers on the vacuum source 40 and allows it to operate for an interval of time, i.e., 5 minutes, the interval being timed using a timing device. Upon completion of the 5 minute interval, operator powers off vacuum source 40. Operator then removes the sample cassette 20 from the first end of the first length of flexible tubing 24, and removably connects the first end of the first length of flexible tubing 24 to the inlet 22 of an unused sample cassette 20 so as to form an airtight seal therebetween.

Operator next stations the system 10 to a second location, i.e., outdoors in the event first sample was collected indoors, and vice-versa where first sample was collected outdoors. Operator then powers on the vacuum source 40 and allows it to operate for an interval of time, i.e., 5 minutes, the interval being timed using a timing device. Upon completion of the 5 minute interval, operator powers off vacuum source 40. Operator then removes the sample cassette 20 from the first end of the first length of flexible tubing 24. Finally, operator forwards both sample cassettes 20 utilized in the two sampling locations to a lab in order that they may be properly analyzed.

Referring now to FIGS. 1 and 5, another alternate embodiment is disclosed wherein the system 10 of the present invention includes a timing device 90 integrated therewith. The timing device 90, according to one embodiment of the present invention, is shown herein as a stop watch 92 formed integral to or suitably attached to the adapter 30. While the timing device 90 may be positioned at other locations about the system 10, the timing device 90 is preferably located proximal the vacuum source 40. Although the timing device 90 is illustrated herein as a stop watch 92, other timing devices and timepieces are contemplated and therefore within the scope and spirit of the present invention.

The alternate embodiment may further include an environmental sensor(s) for detecting and/or measuring relevant environmental factors such as humidity, current time, pressure, and temperature.

Optionally, it is further envisioned that a second alternate embodiment of the present invention may beneficially include sensors which communicate with a control to cause a sample to be collected in response to an event that is detected by the sensors (i.e., one or more sensors). For example, an archival system may be mounted in a residence or commercial facility, to generate an archival record of mold spore elevation. Such a system might be equipped with a mold spore monitor, and when levels of mold spores achieve a predetermined level, a controller (based on sensor data from the sensors) can be programmed to initiate a sampling event, to actuate vacuum source 40 to collect samples on the collection surface 23a of sample cassette 20 for later analysis in response to the sensor readings. Such sensors can be used to measure relevant environmental factors that include, but are not limited to, time, pressure, humidity, temperature, particulate and/or microorganism count, and presence of a particular target bio-molecule (such as particular cell types, pathogens, and toxins). Based on the detection of a specific environmental factor by such a sensor, or in accord with a sampling protocol programmed into the control, one or more of the following functions can be executed by the control: generate a record of the environmental conditions at the time of detection; control the operation of any system components whose performance depends on a measured environmental parameters; manipulate a programmed sampling protocol based on measured environmental factors; and produce an alert signal to notify an operator or operator of an important change in the environmental conditions (as determined by programmed control parameters).

A timer may be included to provide a timing signal to the control. Depending on the type of computing device (or logical circuit) employed for the control, a timer may not be required for this embodiment. Many computing devices do not require a separate timer, and in its simplest form, the control may itself comprise a timer or timing integrated circuit.

Finally, referring to FIGS. 1-5, and 10, the system 10 of the present invention is intended to be made commercially available as a kit, wherein kit 140 comprises a package or housing 142 for housing a number of sample cassettes 20, a first length of flexible tubing 24, an adapter 30 and/or 30a, a second length of flexible tubing 50, a fitting 54, a vacuum nozzle adapter 60 and/or 60a, and an instruction leaflet 144. The housing 142 comprises a plurality of coasters or wheels, and a telescopic handle. The housing 142 further comprises a plurality of drawers or compartments dimensioned for retaining kit elements.

Figure 10:
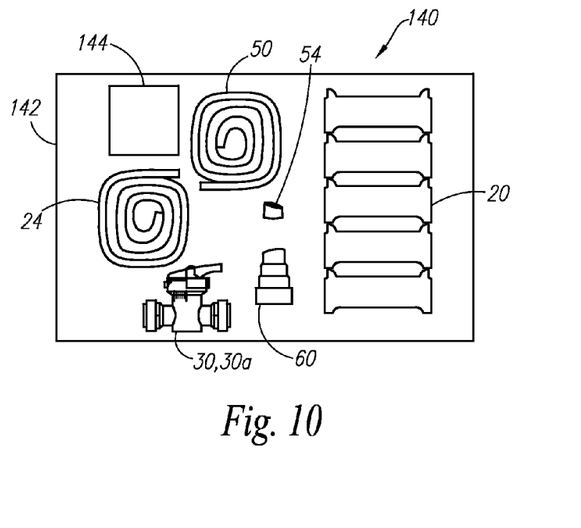
FIG. 10 illustrates a kit, according to one embodiment of the present invention.

It is envisioned kit 140 may further comprise a vacuum source 40, support mechanism 70 and/or 70a, bracket 78 and/or support bracket 110, rod 72 and/or 72a, seal mechanism 100, guide 75 and/or 75a, vacuum rate indicator 200, air flow rate sensor 220, transceiver 222, indicator drive 206, display panel 208, and at least one environmental sensor 320.

It is envisioned that the various embodiments, as separately disclosed, are interchangeable in various aspects, so that elements of one embodiment may be incorporated into one or more of the other embodiments, and that specific positioning of individual elements may necessitate other arrangements not specifically disclosed to accommodate performance requirements or spatial considerations.

It is to be understood that the embodiments and claims are not limited in its application to the details of construction and arrangement of the components set forth in the description and illustrated in the drawings. Rather, the description and the drawings provide examples of the embodiments envisioned, but the claims are limited to the specific embodiments. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the U.S. Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. It is intended that the application is defined by the claims appended hereto.

What is claimed is:

1. A support mechanism for supporting an airborne particle and microorganism sample cassette and a length of flexible tubing in an elevationally-suspended manner above ground during a sample collection interval, the support mechanism comprising:
   a linearly elongated rod having an upper end opposing a lower end, the lower end is curved so as to define an upwardly projecting arcuate shape;
   an annular pin mounted radially to the upper end of the rod, the annular pin having an eye functioning as a guide through which an upper end of a first length of the flexible tubing passes and is supported thereby;
   a bracket, wherein the bracket comprises a generally planar body having a front surface opposing a rear surface, and an upper horizontal, incurvate edge and a lower horizontal, incurvate edge, the upper horizontal, incurvate edge forms a window edge receiving cavity, the window edge receiving cavity receives an outer window edge of a motor vehicle in a snug fit manner, the lower horizontal, incurvate edge forms a bulbous abutment for engagement against an outer surface of a window of the motor vehicle, the rear surface and the lower horizontal, incurvate edge are joined integrally by a flat interface; and
   a seal mechanism, the seal mechanism comprises an elongated configuration constructed of a resiliently compliant material, the seal mechanism includes an upper surface having an elongated slit extending a longitudinal length theredown, the slit snugly receives and conforms to a door outer window edge of a motor vehicle, and wherein the seal mechanism further comprises an aperture defined through a lateral sidewall thereof, the aperture being oriented transverse to the slit, wherein the first length of the flexible tubing is inserted through the aperture, the first length of the flexible tubing is supported by the seal mechanism via the aperture, the seal mechanism engages intimately an entire outer edge of the motor vehicle window, whereupon the motor vehicle window is raised until the seal mechanism forms a seal around the motor vehicle window frame.

2. The support mechanism of claim 1, wherein the bracket is constructed of a flexible, semi-soft rubber or plastic material, the construction material preferably being a non-skid material facilitating frictional grip by the bracket to the window and which prevents scratches and other damage to the motor vehicle window during installation and use.

* * * * *